United States Patent [19]

Hupe et al.

[11] Patent Number: 6,008,220
[45] Date of Patent: Dec. 28, 1999

[54] AROMATIC KETO-ACIDS AND THEIR DERIVATIVES AS INHIBITORS OF MATRIX METALLOPROTEINASES

[75] Inventors: Donald Hupe; Linda Lea Johnson, both of Ann Arbor; Daniel Fred Ortwine, Saline; Claude Forsey Purchase, Jr., Ann Arbor; Andrew David White, Lakeland; Qi-Zhuang Ye, Ann Arbor, all of Mich.

[73] Assignee: Warner Lambert Company, Morris Plains, N.J.

[21] Appl. No.: 09/077,715

[22] PCT Filed: Nov. 27, 1996

[86] PCT No.: PCT/US96/18925

§ 371 Date: Jun. 8, 1998

§ 102(e) Date: Jun. 8, 1998

[87] PCT Pub. No.: WO97/23459

PCT Pub. Date: Jul. 3, 1997

Related U.S. Application Data

[60] Provisional application No. 60/009,489, Dec. 22, 1995.

[51] Int. Cl.⁶ .............. A61K 31/445; A61K 31/495; C07D 211/34; C07D 241/04
[52] U.S. Cl. ............ 514/252; 546/229; 546/230; 546/231; 546/232; 546/234; 546/235; 546/236; 546/237; 546/239; 546/240

[58] Field of Search ............... 546/205, 229, 546/230, 231, 232, 234, 236, 235, 237, 239, 240, 199, 201, 208, 213, 214, 194; 514/317, 319, 318, 331, 322, 323, 256, 326, 252, 253; 544/336, 335, 238, 295, 296

[56] References Cited

FOREIGN PATENT DOCUMENTS

96/33172  10/1996  WIPO.
98/25597   6/1998  WIPO.
98/26773   6/1998  WIPO.

*Primary Examiner*—Mukund J. Shah
*Assistant Examiner*—Ann M. Kessinger
*Attorney, Agent, or Firm*—Francis J. Tinney

[57] ABSTRACT

Aromatic keto-acid compounds and derivatives are described as well as methods for the preparation and pharmaceutical compositions of same, which are useful as inhibitors of matrix metalloproteinases, particularly gelatinase A (72 kD gelatinase) and stromelysin-1 and for the treatment of multiple sclerosis, atherosclerotic plaque rupture, aortic aneurism, heart failure, restenosis, periodontal disease, corneal ulceration, treatment of burns, decubital ulcers, wound healing, cancer, arthrities, or other autoimmune or inflammatory disorders dependent upon tissue invasion by leukocytes.

12 Claims, No Drawings

6,008,220

AROMATIC KETO-ACIDS AND THEIR DERIVATIVES AS INHIBITORS OF MATRIX METALLOPROTEINASES

This application is a 371 of PCT/US96/18924 filed Nov. 27, 1996, which claims benefit of U.S. Provisional Application Ser. No. 60/009,489 filed Dec. 22, 1995.

BACKGROUND OF THE INVENTION

The present invention relates to novel aromatic keto-acid compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (72 kDa gelatinase) and stromelysin-1. More particularly, the novel compounds of the present invention are useful in the treatment of atherosclerotic plaque rupture, aortic aneurism, heart failure, restenosis, periodontal disease, corneal ulceration, treatment of burns, decubital ulcers, wound repair, cancer, arthritis, multiple sclerosis, and other autoimmune or inflammatory disorders dependent on the tissue invasion of leukocytes or other activated migrating cells.

Gelatinase A and stromelysin-1 are members of the matrix metalloproteinase (MMP) family (Woessner J. F., *FASEB J.* 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C. *J. Biol. Chem.*, 1994;269:16766–16773), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is the focal point for inhibitor design. The modification of substrates by introducing chelating groups has generated potent inhibitors such as peptide hydroxymates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.*, 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., Weber K. T., "Activated myocardial collagenase in idiopathic dilated cardiomyopathy", *Clin. Res.*, 1993;41:660A; Tyagi S. C., Reddy H. K., Voelker D., Tjara I. E., Weber K. T., "Myocardial collagenase in failing human heart", *Clin. Res.*, 1993;41:681A). Animal models of heart failure have shown that the induction of gelatinase is important in cardiac dilation (Armstrong P. W., Moe G. W., Howard R. J., Grima E. A., Cruz T. F., "Structural remodeling in heart failure: gelatinase induction", *Can. J. Cardiol.*, 1994;10:214–220), and cardiac dilation precedes profound deficits in cardiac function (Sabbah H. N., Kono T., Stein P. D., Mancini G. B., Goldstein S., "Left ventricular shape changes during the course of evolving heart failure", *Am. J. Physiol.*, 1992;263:H266–H270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., Reidy M., "Smooth muscle cell migration and matrix metalloproteinase expression after arterial injury in the rat", *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSCMs underwent the transition from a quiescent state to a proliferating, motile phenotype after injury to the vessel (Pauly R. R., Passaniti A., Bilato C., Monticone R., Cheng L., Papadopoulos N., Gluzband Y. A., Smith L., Weinstein C., Lakatta E., Crow M. T., "Migration of cultured vascular smooth muscle cells through a basement membrane barrier requires type IV collagenase activity and is inhibited by cellular differentiation", *Circulation Research*, 1994;75:41–54).

Collagenase and stromelysin activities have been demonstrated in fibroblasts isolated from inflamed gingiva (Uitto V. J., Applegren R., Robinson P. J., "Collagenase and neutral metalloproteinase activity in extracts from inflamed human gingiva", *J. Periodontal Res.*, 1981;16:417–424), and enzyme levels have been correlated to the severity of gum disease (Overall C. M., Wiebkin O. W., Thonard J. C., "Demonstrations of tissue collagenase activity in vivo and its relationship to inflammation severity in human gingiva", *J. Periodontal Res.*, 1987;22:81–88). Proteolytic degradation of extracellular matrix has been observed in corneal ulceration following alkali burns (Brown S. I., Weller C. A., Wasserman H. E., "Collagenolytic activity of alkali burned corneas", Arch. Ophthalmol., 1969;81:370–373). Thiol-containing peptides inhibit the collagenase isolated from alkali-burned rabbit corneas (Burns F. R., Stack M. S., Gray R. D., Paterson C. A., Invest. Ophthalmol., 1989;30:1569–1575).

Stromelysin is produced by basal keratinocytes in a variety of chronic ulcers (Saarialho-Kere U. K., Ulpu K., Pentland A. P., Birkedal-Hansen H., Parks W. O., Welgus H. G., "Distinct Populations of Basal Keratinocytes Express Stromelysin-1 and Stromelysin-2 in Chronic Wounds", J. Clin. Invest., 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies, et al., (Cancer Res., 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., Cancer Res., 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., Cancer Res., 1992;52:701–708). Studies of human cancers have shown that gelatinase A is activated on the invasive tumor cell surface (A. Y. Strongin, B. L. Marmer, G. A. Grant, and G. I. Goldberg, J. Biol. Chem., 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., Cancer Res., 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., Journal of the National Cancer Institute, 1995;87:293 and Benelli R., Adatia R., Ensoli B., Stetler-Stevenson W. G., Santi L., and Albini A, Oncology Research, 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", Arthritis Rheum., 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", J. Rheumatol., 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxamate could prevent the formation of both fragments (Andrews H. J., Plumpton T. A., Harper G. P., and Cawston T. E., Agents Actions, 1992;37:147–154; Ellis A. J., Curry V. A., Powell E. K., and Cawston T. E., Biochem. Biophys. Res. Commun., 1994;201:94–101).

Gijbels, et al., (J. Clin. Invest., 1994;94:2177–2182) recently described a peptide hydroxamate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent", J. Cell Biology, 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

We have identified a series of aromatic keto-acid compounds and derivatives that are inhibitors of matrix metalloproteinases, particularly stromelysin-1 and gelatinase A, and thus useful as agents for the treatment of multiple sclerosis, atherosclerotic plaque rupture, restenosis, aortic aneurism, heart failure, periodontal disease, corneal ulceration, treatment of burns, decubital ulcers, wound repair, cancer, arthritis, or other autoimmune or inflammatory diseases dependent upon tissue invasion by leukocytes.

SUMMARY OF THE INVENTION

Accordingly, the present invention is a compound of Formula I

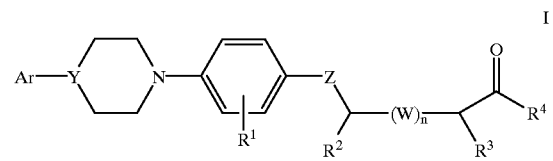

Ar is selected from phenyl,
  phenyl substituted with
    alkyl,
    $NO_2$,
    halogen,
    $OR^5$ wherein $R^5$ is hydrogen or alkyl,
    CN,
    $CO_2R^5$ wherein $R^5$ is as defined above,
    $SO_3R^5$ wherein $R^5$ is as defined above,
    CHO,
    $COR^5$ wherein $R^5$ is as defined above,
    $CONHR^5$ wherein $R^5$ is as defined above, or
    $NHCOR^5$ wherein $R^5$ is as defined above,
  2-naphthyl, or
  heteroaryl;

$R^1$ is selected from hydrogen,
methyl,
ethyl,
$NO_2$,
halogen,
$OR^5$ wherein $R^5$ is as defined above,
CN,
$CO_2R^5$ wherein $R^5$ is as defined above,
$SO_3R^5$ wherein $R^5$ is as defined above,
CHO, or
$COR^5$ wherein $R^5$ is as defined above;

$R^2$ and $R^3$ are the same or different and independently selected from hydrogen,
alkyl,
—$(CH_2)_v$-aryl wherein v is an integer from 1 to 5,
—$(CH_2)_v$-heteroaryl wherein v is as defined above,
—$(CH_2)_v$-cycloalkyl wherein v is as defined above,
—$(CH_2)_p$—X—$(CH_2)_q$-aryl wherein X is O or S and p and q is each zero or an integer of 1 to 5, and the sum of p+q is not greater than an integer of 5,
—$(CH_2)_p$—X—$(CH_2)_q$-heteroaryl wherein X, p, and q are as defined above,
—$(CH_2)_tNR^6R^{6a}$, wherein t is zero or an integer of from 1 to 9 and $R^6$ and $R^{6a}$ are each the same or different and are as defined above for $R^5$,
—$(CH_2)_vSR^5$, wherein v and $R^5$ are as defined above,
—$(CH_2)_vCO_2R^5$, wherein v and $R^5$ are as defined above, or
—$(CH_2)_vCONR^6R^{6a}$, wherein $R^6$ and $R^{6a}$ are the same or different and are as defined above for $R^5$ and v is as defined above;

$R^3$ is additionally —$(CH_2)_rR^7$ wherein r is an integer from 1 to 5 and $R^7$ is 1,3-dihydro-1,3-dioxo-2H-isoindol-2-yl, or 1,3-dihydro-1,3-dioxo-benzo[f]isoindol-2-yl;

Y is CH or N;

Z is 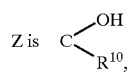

wherein $R^{10}$ is as defined above for $R^2$ and $R^3$, and is independently the same or different from $R^2$ and $R^3$ provided that when Z is

then $R^4$ must be OH,
C=O,
C=$NOR^5$ wherein $R^5$ is as defined above, or
C=N—$NR^6R^{6a}$ wherein $R^6$ and $R^{6a}$ are the same or different and are as defined above for $R^5$;

W is —$CHR^5$ wherein $R^5$ is as defined above;

n is zero or an integer of 1;

$R^4$ is OH,
$NR^6R^{6a}$ wherein $R^6$ and $R^{6a}$ are the same or different and are as defined above for $R^5$, when $R^4$ is $NR^6R^{6a}$ then Z must be C=O or $NHOR^9$ wherein $R^9$ is hydrogen, alkyl, or benzyl;

and corresponding isomers thereof; or a pharmaceutically acceptable salt thereof.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, cancer metastasis, tumor angiogenesis, arthritis, and other inflammatory disorders dependent upon tissue invasion by leukocytes.

A still further embodiment of the present invention is a pharmaceutical composition for administering an effective amount of a compound of Formula I in unit dosage form in the treatment methods mentioned above. Finally, the present invention is directed to methods for production of compounds of Formula I.

DETAILED DESCRIPTION OF THE INVENTION

In the compounds of Formula I, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, $SO_3H$, CHO,

as defined above for alkyl,

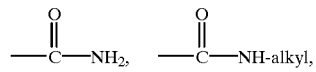

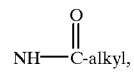

as defined above for alkyl,

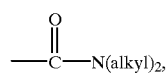

as defined above for alkyl, —$(CH_2)_{n^2}$—$NH_2$ wherein $n^2$ is an integer of 1 to 5, —$(CH_2)_{n^2}$—NH-alkyl as defined above for alkyl and $n^2$, —$(CH_2)_{n^2}$—$N(alkyl)_2$ as defined above for alkyl and $n^2$.

The term "heteroaryl" means a heteroaromatic radical and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl.

"Halogen" is fluorine, chlorine, bromine, or iodine.

Phenyl is abbreviated "Ph".

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloro-procaine, choline, diethanolamine, dicyclohexylamine, ethylenediamine, N-methylglucamine, and procaine (see, for example, Berge S. M., et al., "Pharmaceutical Salts," *J. of Pharma Sci.*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In one embodiment of the invention, a preferred compound of Formula I is one wherein Ar is phenyl; and corresponding isomers thereof; or a pharmaceutically acceptable salt thereof.

Another preferred compound of Formula I of this embodiment is one wherein Y is CH; and corresponding isomers thereof; or a pharmaceutically acceptable salt thereof.

Another preferred compound of Formula I of this embodiment is one wherein Z is C=O; and corresponding isomers thereof; or a pharmaceutically acceptable salt thereof.

Another preferred compound of Formula I of this embodiment is one wherein n is zero; and corresponding isomers thereof; or a pharmaceutically acceptable salt thereof.

Another preferred compound of Formula I of this embodiment is one wherein $R^1$, $R^2$, and $R^3$ are hydrogen; and corresponding isomers thereof; or a pharmaceutically acceptable salt thereof.

Another preferred compound of Formula I of this embodiment is one wherein $R^4$ is OH; and corresponding isomers thereof; or a pharmaceutically acceptable salt thereof.

In another embodiment of the invention, a preferred compound of Formula I is one wherein Z is C=NOR$^5$; and corresponding isomers thereof; or a pharmaceutically acceptable salt, thereof.

Another preferred compound of Formula I of this embodiment is one wherein Y is N; and corresponding isomers thereof; or pharmaceutically acceptable salt thereof.

Another preferred compound of Formula I of this embodiment is one wherein n is 1; and corresponding isomers thereof; or a pharmaceutically acceptable salt thereof.

Another preferred compound of Formula I of this embodiment is one wherein Ar is phenyl; Z is C=O; Y is CH; and $R^4$ is OH; and corresponding isomers thereof; or a pharmaceutically acceptable salt thereof.

Another preferred compound of Formula I of this embodiment is one wherein Ar is phenyl; Z is C=O; $R^1$, $R^2$, and $R^3$ are hydrogen; and $R^4$ is OH; and corresponding isomers thereof, or a pharmaceutically acceptable salt thereof.

Another preferred compound of Formula I of this embodiment is one wherein Ar is phenyl; Z is C=O; $R^1$, $R^2$, and $R^3$ are hydrogen; $R^4$ is OH; and n is zero; and corresponding isomers thereof; or a pharmaceutically acceptable salt thereof.

Another preferred compound of Formula I of this embodiment is one wherein Ar is phenyl; Z is C=O; $R^1$, $R^2$, and $R^3$ are hydrogen; $R^4$ is NHOH; and n is zero; and corresponding isomers thereof; or a pharmaceutically acceptable salt thereof.

Another preferred compound of Formula I of this embodiment is one wherein Ar is phenyl; Z is C=N—OH; $R^1$, $R^2$, and $R^3$ are hydrogen; $R^4$ is OH; and n is zero; and corresponding isomers thereof; or a pharmaceutically acceptable salt thereof.

Another preferred compound of Formula I of this embodiment is one wherein $R^1$ and $R^2$ are hydrogen; and corresponding isomers thereof, or a pharmaceutically acceptable salt thereof.

Particularly valuable is a compound selected from the group consisting of:

4-Oxo-4-[4-(4-phenyl-piperidin-1-yl)-phenyl]-butyric acid;

4-Oxo-4-[4-(4-phenyl-piperidin-1-yl)-phenyl]-butyric acid, potassium salt;

N-Hydroxy-4-oxo-4-[4-(4-phenyl-piperidin-1-yl)-phenyl]-butyramide;

E/Z-4-Hydroxyimino-4-[4-(4-phenyl-piperidin-1-yl)-phenyl]-butyric acid;

E/Z-4-Benzyloxyimino-4-[4-(4-phenyl-piperidin-1-yl)-phenyl]-butyric acid;

4-Oxo-4-[4-(4-phenyl-piperazin-1-yl)-phenyl]-butyric acid; and (±)3-Methyl-5-oxo-5-[4-(4-phenyl-piperidin-1-yl)-phenyl]-pentanoic acid; and corresponding isomers thereof; or a pharmaceutically acceptable salt thereof.

More particularly valuable are 4-oxo-4-[4-(4-phenyl-piperidin-1-yl)-phenyl]-butyric acid; N-hydroxy-4-oxo-4-[4-(4-phenyl-piperidin- 1-yl)-phenyl]-butyramide; E/Z-4-hydroxyimino-4-[4-(4-phenyl-piperidin-1-yl)-phenyl]-butyric acid; and corresponding isomers thereof; or a pharmaceutically acceptable salt thereof.

The compounds of Formula I are valuable inhibitors of gelatinase A and/or stromelysin-1. It has been shown previously that inhibitors of matrix metalloproteinases have efficacy in models of disease states like arthritis and metastasis that depend on modification of the extracellular matrix.

In vitro experiments were carried out which demonstrate the efficacy of compounds of Formula I as potent and specific inhibitors of gelatinase A and stromelysin-1. Experiments were carried out with the catalytic domains of the proteinases. Table I shows the activity of Examples 1–7 versus GCD (recombinant gelatinase A catalytic domain) and SCD (stromelysin-1 catalytic domain). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*", *Biochemistry*, 1992;31:11231–11235).

TABLE I

| Example | $IC_{50}$ (μM) | |
| --- | --- | --- |
| | SCD | GCD |
| 1 | 0.14 | 1.3 |
| 2 | 0.08 | 0.56 |
| 3 | 0.02 | 0.04 |
| 4 | 0.02 | 0.15 |
| 5 | 2.9 | 6.3 |
| 6 | 0.25 | 1.6 |
| 7 | 0.40 | 14 |

The following list contains abbreviations and acronyms used within the schemes and text:

| AcOH | Acetic acid |
| --- | --- |
| CDI | Carbonyl diimidazole |
| DCC | Dicyclohexylcarbodiimide |
| DCM | Dichloromethane |
| kDa | Kilo dalton |
| DMF | Dimethyl formamide |
| DMSO | Dimethylsulfoxide |
| EtOH | Ethanol |
| HCl | Hydrochloric acid |
| HPLC | High performance liquid chromatography |
| $IC_{50}$ | Concentration of compound required to inhibit 50% of matrix metalloproteinase activity |
| KHMDS | Potassium hexamethyldisilazide |
| KOH | Potassium hydroxide |
| $NaBH_4$ | Sodium borohydride |
| NaH | Sodium hydride |
| LiOH | Lithium hydroxide |
| MeOH | Methanol |
| mRNA | Messenger ribonucleic acid |
| n-BuLi | n-butyl lithium |
| Pd/C | Palladium on carbon |
| psi | Pounds per square inch |
| Py | Pyridine |
| THF | Tetrahydrofuran |
| TIMPs | Tissue inhibitors of metalloproteinases |
| TMSCl | Trimethylsilyl chloride |
| TSOH | Para-toluenesulfonic acid |

A compound of Formula I can be made by one of three general routes, as set forth in Scheme 1.

Route A involves reaction of a compound of Formula II with a compound of Formula III under basic conditions, for example, $K_2CO_3$ in a polar solvent such as DMSO, to afford a compound of Formula Ia, Formula I where $R^4$=OH.

Route B involves a Friedel-Crafts acylation of a compound of Formula IV with a compound of Formula V as an acid chloride derivative or Va as an anhydride either neat or in an inert solvent such as, for example, dichloromethane, or nitrobenzene, and the like in the presence of a Lewis acid such as $FeCl_3$, $AlCl_3$, $ZnCl_2$, and the like at about −40° C. to 150° C. to afford a compound of Formula Ia, Formula I where $R^4$=OH.

Route C involves reaction of a compound of Formula VI, wherein M is Li, Mg-halogen or $(Cu\text{-halogen})_{1/2}$ with a compound of Formula VII wherein L is halogen, or —N(Me)OMe, and Ar, W, n, $R^2$, and $R^3$ are as defined above, and $R^4$ is a suitably protected ester, e.g., benzyl, using conventional methodology such as, for example, methodology described by Nahm S. and Weinreb S. M., *Tetrahedron Letters*, 1981;22:3815 to afford a compound of Formula Ia, Formula I where $R^4$=OH.

Specific compounds of the present invention can be prepared by various routes, all of which are generally known in the art. Compounds of Formula I, wherein n=0, Ar and Z are defined as in Formula I, and $R^1$, $R^2$, and $R^3$ are hydrogen, Y=CH, and $R^4$ is OH, can be synthesized according to the sequence described in Scheme 2.

An aryl halide (1), wherein halo is defined as iodine, bromine, or chlorine, is reacted with a suitable alkyl lithium such as n-butyl lithium in a suitable solvent such as THF or diethyl ether at temperatures between −80° C. and 25° C., and the resulting product, an aryl lithium, (Scheme 2) is reacted with 1-(phenylmethyl)-4-piperidinone at temperatures between −80° C. and 25° C. to yield the 4-aryl-4-piperidinol (2). The alcohol (2) is dehydrated to yield the 1,2,5,6-tetrahydropyridine (3) as an acid salt by stirring in a suitable solvent such as acetic acid with a strong acid catalyst such as concentrated HCl at temperatures between 20° C. and reflux. The 1,2,5,6-tetrahydro-pyridine (3) is reduced to yield the 4-aryl-piperidine hydrochloride (4) by catalytic reduction using a suitable catalyst such as 10% palladium on carbon and hydrogen gas ($H_2$) at pressures between 10 psi and 100 psi in a suitable solvent such as absolute ethanol, acetic acid, or THF.

The keto-acid (5) is reacted with the 4-aryl-piperidine hydrochloride (4) to yield the diphenyl-piperidine (6) by stirring in a suitable solvent such as dimethylsulfoxide (DMSO) or dimethylformamide (DMF) in the presence of a base such as potassium or sodium carbonate at temperatures between 20° C. and reflux.

The keto-acid (6) can be converted to the oxime-acid (7), keto-hydroxamic acid (9), oxime-hydroxamic acid (12), hydrazone (14), or alcohol derivative Z is C(H)OH (13) by employing the methods outlined in Scheme 3.

The keto-acid (6) is reacted with hydroxylamine hydrochloride ($H_2NOH \cdot HCl$) to yield the oxime-acid (7) by stirring in a suitable solvent such as ethanol in the presence of a mild base such as sodium carbonate ($Na_2CO_3$) or pyridine at temperatures between 25° C. and reflux as shown in Scheme 3. In a similar fashion, O-substituted compounds such as O-benzylhydroxylamine react to yield the O-substituted oximes.

The keto-acid (6) can be reacted with an O-protected hydroxylamine such as O-benzylhydroxylamine hydrochloride ($H_2NOCH_2C_6H_5 \cdot HCl$) to yield the keto-O-protected hydroxamic acid (8) by first stirring the keto-acid (6) with a coupling agent such as 1,1'-carbonyldiimidazole (CDI) or N,N'-dicyclohexylcarbodiimide (DCC) in a suitable solvent such as THF, DCM, or DMF at temperatures between 0° C. and 100° C. The keto-O-protected hydroxamic acid (8) can be reduced to yield the keto-hydroxamic acid (9) by catalytic reduction using hydrogen gas at pressures between 10 psi and 100 psi and a suitable catalyst such as 10% palladium on barium sulfate in a suitable solvent such as THF or ethanol.

The keto-O-protected hydroxamic acid (8) can be reacted with hydroxylamine to yield the oxime-O-protected hydroxamic acid (11) by employing conditions similar to those described previously for compound (7). The oxime-O-protected hydroxamic acid (11) can be reduced to yield the oxime-hydroxamic acid (12) by employing conditions similar to those described for compound (9).

The alcohol derivative (13) can be synthesized via reduction of (6) under standard conditions, for example with $NaBH_4$ in a suitable solvent such as ethanol.

The alcohol derivative (13a) can be synthesized by addition of a Grignard reagent of the formula $R^{10}MgBr$ to the ketone (6) under standard conditions. For instance two mole equivalents of the Grignard can be reacted with one mole equivalent of (6) in a suitable solvent such as THF or diethyl ether at temperatures between −78° C. and 25° C.

The Grignard reagent $R^{10}MgBr$ can be prepared in situ by reacting an alkyl halide of the formula $R^{10}Br$ with magnesium metal in a suitable solvent such as THF or diethyl ether at temperatures between 0° C. and reflux. The alkyl halide of formula $R^{10}Br$ is either commercially available or can be prepared by methods known by one skilled in the art.

The ketone (6) can be reacted with a hydrazine of formula $H_2NNR^6R^{6a}$, wherein $R^6$ and $R^{6a}$ are as defined in Formula I, to yield the hydrazone (14) under standard conditions such as refluxing in suitable solvent such as methanol or ethanol.

The keto acid (6) is reacted with amine ($R^6R^{6a}NH$) to yield the amide 13b by first stirring the keto acid (6) with a coupling agent such as CDI or DCC in a suitable solvent such as THF, DCM, or DMF at temperatures between 0° C. and 100° C.

Compounds of Formula I wherein n=0, Ar is as defined in Formula I, and $R^1$, $R^2$, and $R^3$ are hydrogen, Y=N, and $R^4$ is OH can be synthesized according to the sequence described in Scheme 4.

Aniline derivatives (15) are condensed with bis(2-chloroethyl)amine hydrochloride (16) in a solvent such as chlorobenzene at temperatures between 95° C. and reflux to furnish the arylpiperazine hydrochloride (17). The aryl piperazine (17) is reacted with the aryl fluoride (5) in a manner similar to that described for compound (6) in Scheme 2 to obtain the corresponding piperazine (18).

The compounds of Formula I wherein n=1, $R^1$, $R^2$, and $R^3$ are hydrogen, $R^4$ is OH, and Ar and Y are as defined in Formula I can be prepared as set forth in Scheme 5.

In Scheme 5, the phosphonoacetate (19) is reacted with an aldehyde of formula $R^8CHO$ to yield the 2-alkenoic ester (20) by stirring in a suitable solvent such as tetrahydrofuran (THF) in the presence of a strong base such as sodium hydride or lithium diisopropylamide at temperatures between 0° C. and reflux. The 2-alkenoic ester (20) is reacted with the malonate of formula $CH_2(CO_2CH_2CH_3)_2$ to yield the triester (21) by stirring in a suitable solvent such as absolute ethanol in the presence of a strong base such as sodium ethoxide at temperatures between 20° C. and reflux. The triester (21) is hydrolyzed and decarboxylated in one pot to yield the diacid (22) by stirring in an aqueous acid such as hydrochloric acid (1 to 12 M) at temperatures between 20° C. and reflux. The diacid (22) is cyclodehydrated to yield the cyclic anhydride (23) by stirring with a suitable dehydrating agent such as acetic anhydride in a suitable solvent such as acetic acid at temperatures between room temperature and reflux. The cyclic anhydride (23) is reacted with a halo-benzene of the formula $C_6H_5$-halo, where halo is fluorine or chlorine, to yield the keto-acid (24) by stirring in a suitable solvent such as dichloromethane or nitrobenzene in the presence of a catalyst such as aluminum chloride ($AlCl_3$) at temperatures between −40° C. and 100° C. The keto-acid (24) is then converted to acid (25) by reaction with either (4) or (17) represented by the general Formula II in a manner similar to that described for compound (6).

Compounds of Formula I wherein n=0, Ar, $R^2$, and $R^3$ are as defined in Formula I, $R^1$ is hydrogen, and $R^4$ is OH can be synthesized according to the sequence described in Scheme 6.

R or S 4-benzyl-2-oxazolidinone is acylated with (26) via deprotonation with a suitable base such as NaH and reaction with the acid chloride (26) to afford a compound of formula (27). The compound of formula (27) is deprotonated with potassium hexamethyldisilazide at −78° C. and reacted with halide (28) at temperatures from −78° C. to room temperature to give a compound of formula (29). Diastereomers of (29) are separated by a suitable method such as column chromatography on silica gel or HPLC, the oxazolidinone is removed with LiOH and hydrogen peroxide to give the carboxylic acid derivative, and the carboxylic acid is converted to an acid chloride with oxalyl chloride in a suitable solvent such as THF to give a compound of formula (30). A compound of formula (30) is reacted with N,O-dimethyl hydroxylamine hydrochloride in the presence of pyridine to afford a compound of formula (31).

Aryl anhydride (23a) is synthesized from an aldehyde of formula ArCHO as set forth in Scheme 5 for compound (23) or from commercially available intermediates corresponding to (20–22). Compound (23a) is condensed with 4-bromoaniline in a suitable solvent such as toluene, at room temperature to reflux. The resulting adduct is cyclized with acetic anhydride in acetic acid to afford imide (32), which is reduced with $LiBH_4$/TMSCl in a solvent such as THF to yield the compound of formula (33). The aryl bromide (33) is reacted with a suitable alkyl lithium such as n-butyl lithium in a suitable solvent such as THF or diethyl ether at temperatures between −80° C. and 25° C., and the resulting product, an aryl lithium, is reacted with Weinreb amide (31) to afford the adduct (34), which is debenzylated under standard conditions such as catalytic reduction using hydrogen gas and a suitable catalyst such as 5% palladium on barium sulfate in a suitable solvent such as THF or ethanol, to afford compounds of formula (35).

Compounds of Formula I, wherein n=0, Ar, and $R^1$, $R^2$, and $R^3$, are as defined in Formula I, and $R^4$ is OH can be synthesized according to the sequence described in Scheme 7.

A compound of formula (36), commercially available or synthesized by methods known in the art, is converted to a compound of formula (37) as described for compound (6) in Scheme (2). The ester (37) is hydrolyzed to the carboxylic acid under standard conditions such as KOH in ethanol, and the acid is reacted with a suitable coupling agent such as carbonyl diimidazole in dichloromethane or THF and N,O-dimethylhydroxylamine to give the amide (38). A compound of formula (38) is reacted with a Grignard reagent of formula $R^2CH_2MgX$ (X=Cl,Br) commercially available or synthesized by standard methods known in the art, in a solvent such as THF or diethyl ether to give a ketone of formula (39). The ketone (39) is converted to the α-bromoketone (40) by reaction with N-bromosuccinimide.

A compound of formula (41) is synthesized via a method analogous to that described for compound (27) from R or S 4-benzyl-2-oxazolidinone. Compound (41) is deprotonated with potassium hexamethyldisilazide and reacted with α-bromoketone (40) to afford compound (42). Diastereomers of (42) are separated by a suitable method such as column chromatography on silica gel or HPLC, and the oxazolidinone is removed with LiOH and hydrogen peroxide to afford compounds of formula (43).

The compounds of formula (18, 25, 35, and 43) shown in Schemes 4, 5, 6, and 7, respectively, can be converted to their corresponding keto-acid derivatives as set forth in Scheme 3 by substituting compounds (18, 25, 35, and 43) for compound (6) in Scheme 3.

The compounds of Formula 1a where $R^2$ or $R^3$ is $NH_2$ are synthesized by general route B depicted in Scheme 1 utilizing Va where $R^2$ or $R^3$ is $NHCOCF_3$ (trifluromethylamide). The amide is then deprotected to afford 1a ($R^2$ or $R^3$ is $NH_2$) under standard conditions such as potassium or sodium carbonate in a suitable solvent such as MeOH or EtOH at temperatures between 0° C. and reflux.

Scheme 1
Route A

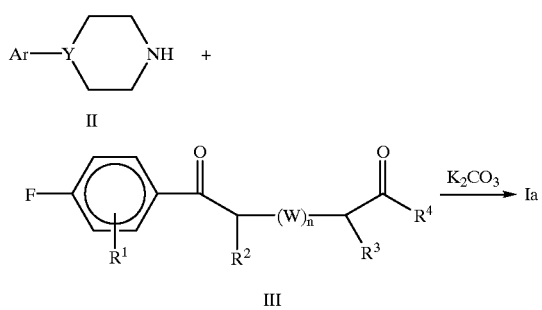

Route B

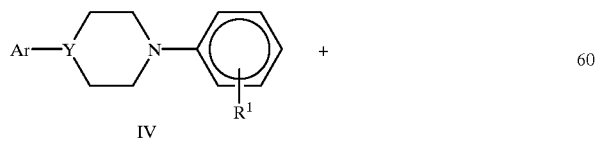

-continued

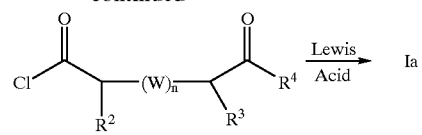

or

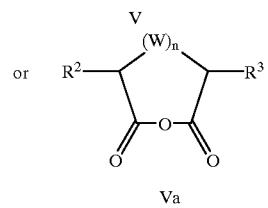

Route C

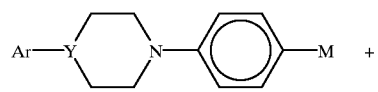

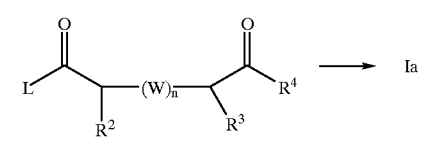

Scheme 2

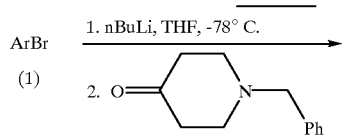

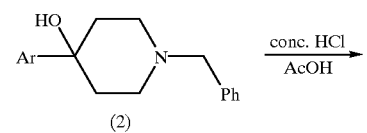

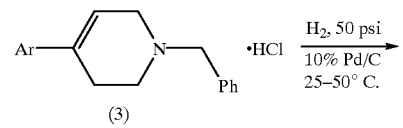

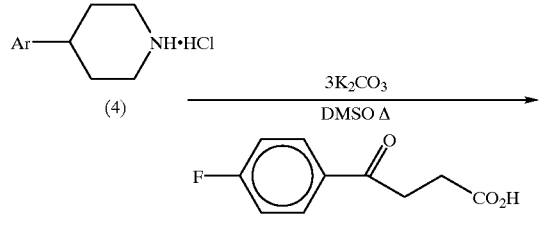

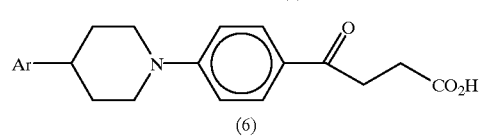

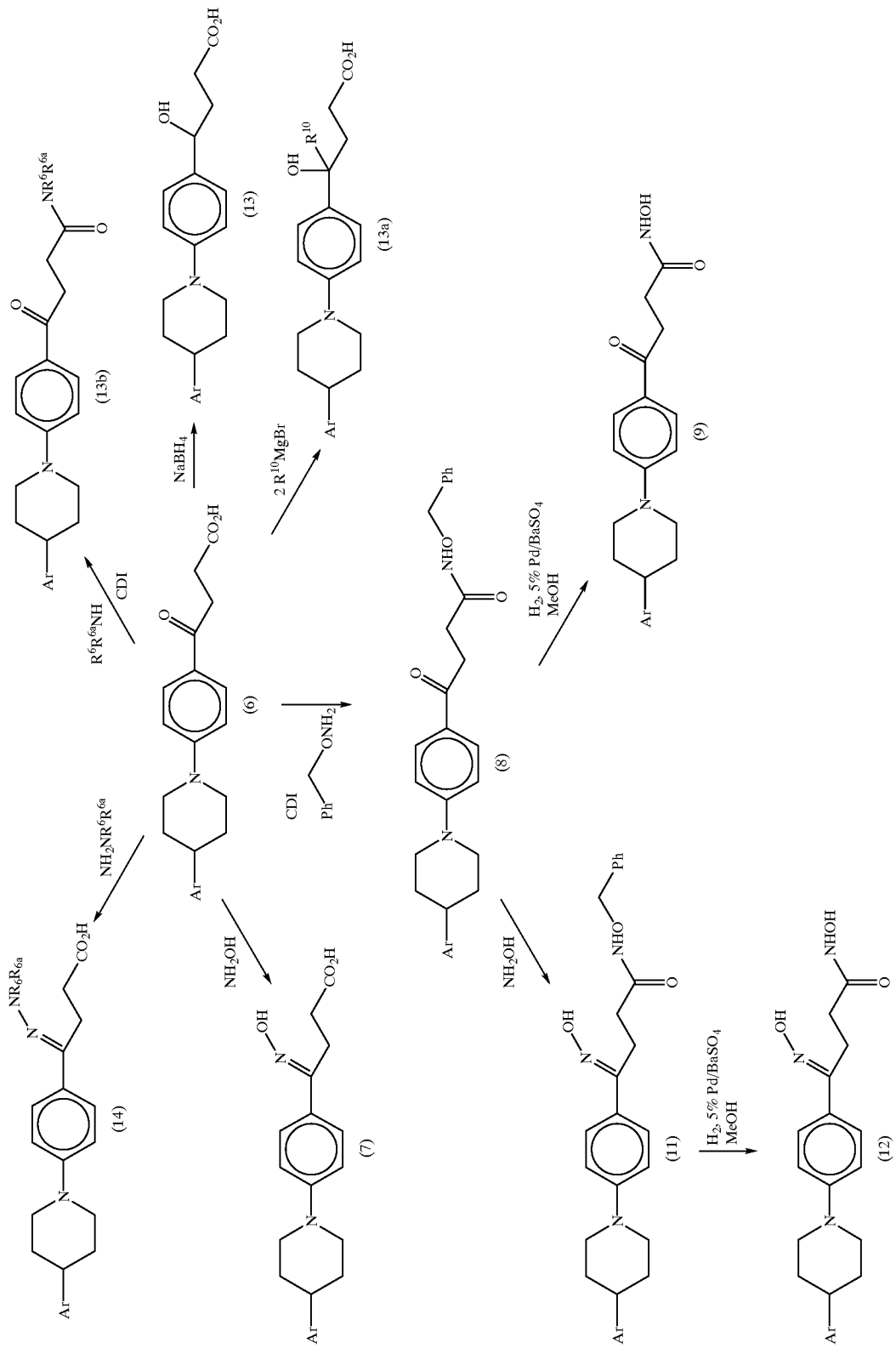

Scheme 4
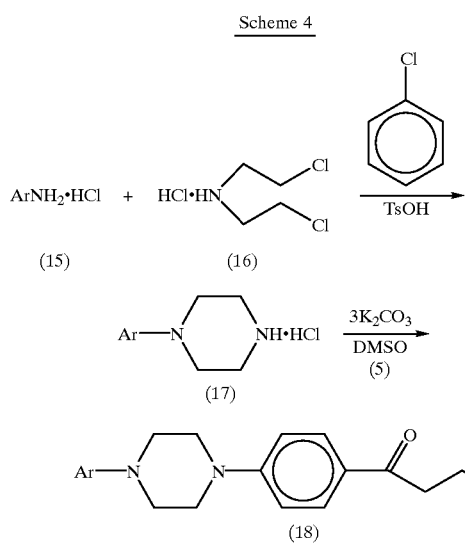
Scheme 5
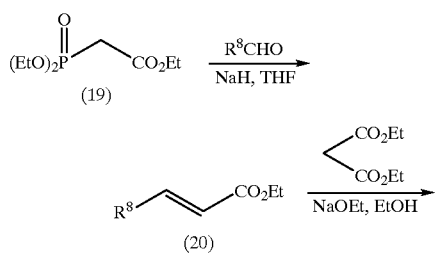
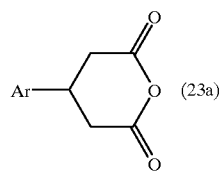
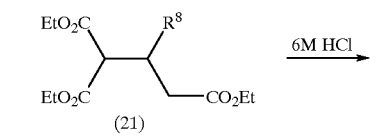
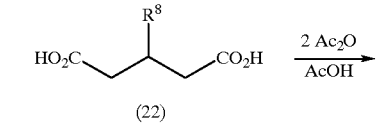
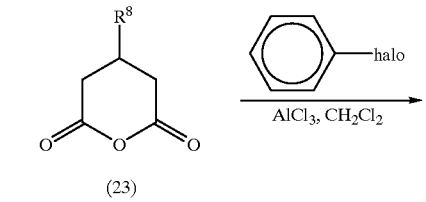
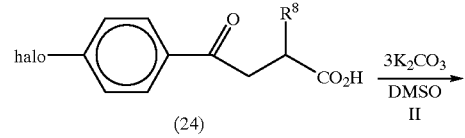
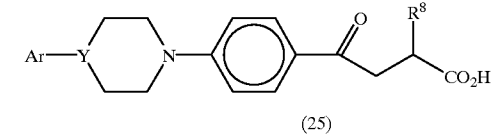
Scheme 6
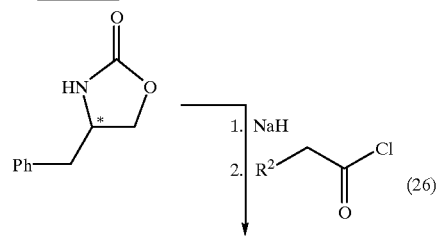
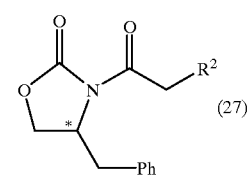
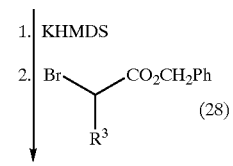

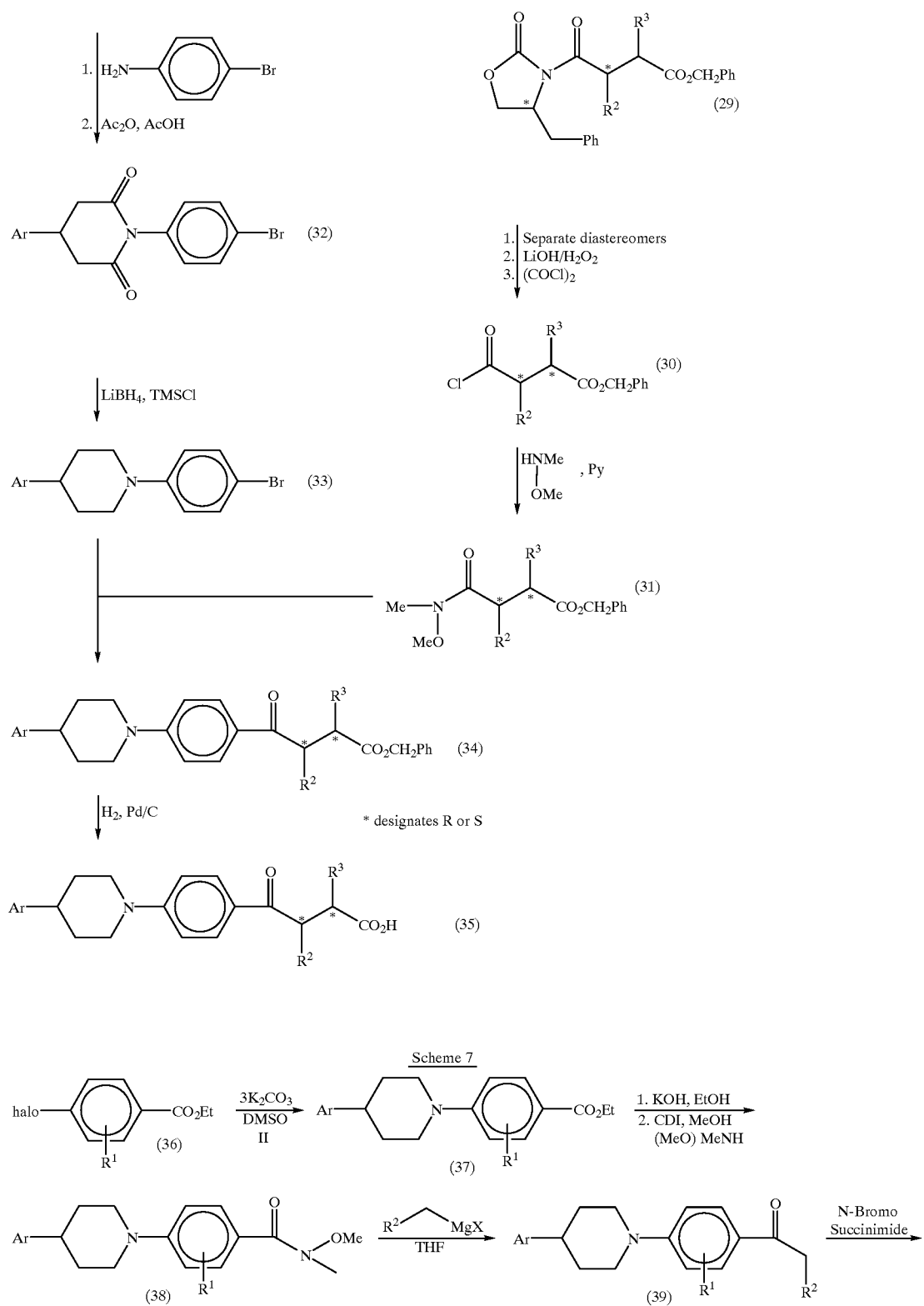

-continued

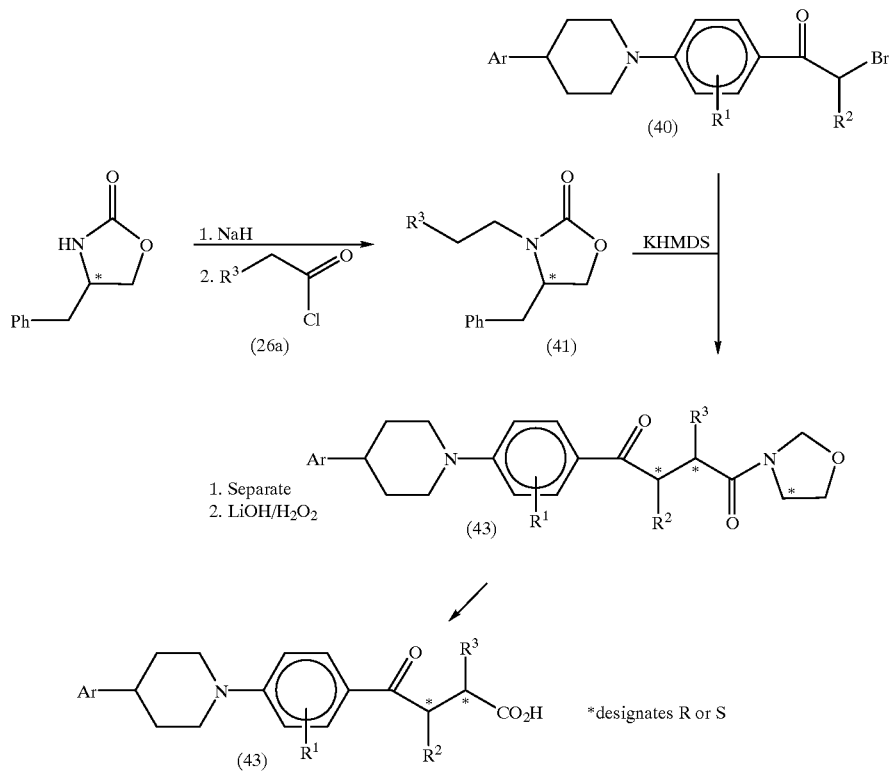

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, treatment of burns, decubital ulcers, wound healing, cancer, arthritis, or other autoimmune or inflammatory disorders dependent upon tissue invasion by leukocytes, the compounds utilized in the pharmaceutical method of this invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

4-Oxo-4-[4-(4-phenyl-piperidin-1-yl)-phenyl]-butyric acid

A stirred mixture of 4-phenyl-piperidine (10.4 g, 0.064 mol), 3-(4-fluorobenzoyl)-propionic acid (12.1 g, 0.062 mol), and potassium carbonate (17.5 g, 0.13 mol) in DMSO (15 mL) was heated under an atmosphere of nitrogen at 120° C. for 18 hours. The mixture was allowed to cool, diluted with water (100 mL), and brought to pH 2 dropwise with 1 M HCl. The resulting solid was filtered, washed with water, and dried in vacuo to yield a pale orange solid as the title compound (11.2 g, %C,H,N found: 74.54, 6.98, 4.07).

EXAMPLE 2

4-Oxo-4-[4-(4-phenyl-piperidin-1-yl)-phenyl]-butyric acid, potassium salt

A stirred mixture of 4-phenyl-piperidine (8.1 g, 0.05 mol), 3-(4-fluorobenzoyl)-propionic acid (9.9 g, 0.05 mol), and potassium carbonate (7.0 g, 0.05 mol) in DMSO (50 mL) was heated under an atmosphere of nitrogen at 120° C. for 18 hours. The mixture was allowed to cool and diluted with water (100 mL). The resulting solid was filtered and washed with water. The resulting solid was recrystalized from boiling methanol and dried in vacuo to yield a pale brown solid as the title compound hydrate [6.6 g, 300 MHz]; $^1$H NMR (DMSO): δ 7.82 (d, 2H, J=8.1 Hz), 7.33–7.20 (m, 5H), 7.01 (d, 2H, J=8.1 Hz), 4.06 (d br, 2H, J=12.9 Hz), 2.97–2.90 (m, 4H), 2.78 (m, 1H), 2.11 (t, 2H, J=7.5 Hz), 1.86 (br d, 2H, J=11.7 Hz), 1.70 (m, 2H)].

EXAMPLE 3

N-Hydroxy-4-oxo-4-[4-(4-phenyl-piperidin-1-yl)-phenyl]-butyramide (a) 4-Oxo-4-[4-(4-phenyl-piperidin-1-yl)-phenyl]-butyric acid (1.0 g, 2.96 mmol) (Example 1) and carbonyldimidazole (0.51 g, 3.11 mmol) were stirred for 18 hours at room temperature under nitrogen. A slurry of O-Benzylhydroxylamine (0.57 g, 3.55 mmol) and triethylamine (0.49 mL, 3.55 mol) in THF (5 mL) was added in one portion and the resulting mixture refluxed for 18 hours, filtered, and washed with THF (50 mL). The filtrate was concentrated and columned on silica gel eluting with 50% ethyl acetate in hexanes to give 4-benzyloxyimino-4-[4-(4-phenyl-piperidin-1-yl)-phenyl]-butyric acid (0.68 g, %C,H,N found: 76.01, 6.89, 6.26).

(b) N-benzyloxyimino-4-[4-(4-phenyl-piperidin-1-yl)-phenyl]-butyric acid (0.41 g, 0.93 mmol) was stirred at room temperature with 5% Pd/BaSO$_4$ (0.04 g) in methanol (50 mL) under 50 psi of H$_2$ for 10 hours. The mixture was filtered and washed with MeOH, and the filtrate was concentrated and triturated with ethyl acetate to yield the title compound as a white solid (0.25 g, %C,H,N found: 71.03, 7.05, 7.65).

EXAMPLE 4

E/Z-4-Hydroxyimino-4-[4-(4-phenyl-piperidin-1-yl)-phenyl]-butyric acid

Sodium carbonate (0.80 g, 5.76 mmol) was added to hydroxylamine hydrochloride (0.80 g, 11.5 mmol) in water (3 mL), and the mixture stirred for 15 minutes with ice cooling. The resulting mixture was added to 4-oxo-4-[4-(4-phenyl-piperidin-1-yl)-phenyl]-butyric acid (2.99 g, 8.86 mmol) (Example 1) in ethanol (50 mL) and the resulting mixture refluxed for 6 hours, concentrated to one-third volume, and allowed to cool. The resulting precipitate was dissolved in hot sodium bicarbonate solution, filtered, and the filtrate acidified with 1M HCl to yield a slurry which was filtered, washed with water, and dried in vacuo to give the title compound as a white solid (1.17 g, %C,H,N found: 71.77, 6.79, 7.88).

EXAMPLE 5

E/Z-4-Benzyloxyimino-4-[4-(4-phenyl-piperidin-1-yl)-phenyl]-butyric acid

The title compound was synthesized (0.33 g, E/Z 10:1, %C,H,N found: 76.01, 7.05, 6.20) using the method of Example 4, substituting O-benzylhydroxylamine for hydroxylamine.

EXAMPLE 6

4-Oxo-4-[4-(4-phenyl-piperazin-1-yl)-phenyl]-butyric acid

The title compound was prepared (0.11 g, 400 MHz) using the method of Example 1 substituting N-phenylpiperazine for 4-phenylpiperidine.

$^1$H NMR (DMSO): δ 7.86 (d, 2H, J=8.8 Hz), 7.26–7.22 (m, 2H), 7.06–6.99 (m, 4H), 6.81 (t, 1H, J=7.2 Hz), 3.50–3.45 (m, 2H), 3.29–3.26 (m, 2H), 3.12 (t, 2H, J=6.0 Hz), 2.5 (t, 2H).

EXAMPLE 7

(±)3-Methyl-5-oxo-5-[4-(4-phenyl-piperidin-1-yl)-phenyl]-pentanoic acid

A stirred mixture of 4-phenylpiperidine (0.161 g, 1.00 mmol), (±)3-methyl-5-(4-chloro-phenyl)-pentanoic acid (0.241 g, 1.00 mol), and potassium carbonate (0.276 g, 2.00 mol) in dry dimethyl sulfoxide was heated in a sand bath (160° C.) under nitrogen for 15 hours. The mixture was cooled and diluted with water. The aqueous solution was filtered, and the filtrate was acidified with concentrated hydrochloric acid to pH=6. A brown gum formed. The liquid was decanted, and the residue was chromatographed on silica gel (38 g, 230–400 mesh) eluting with dichloromethane-methanol (20:1, 15×40 mL). Fractions containing product were combined and rotary evaporated to give a brown glass. The glass was crystallized from methanol after a hot gravity filtration to give the title compound as a tan solid; yield 0.0360 g (10%, mp=134–135° C.).

We claim:

1. A compound of Formula I

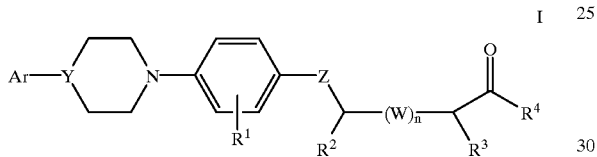

wherein Ar is selected from phenyl,
phenyl substituted with
  alkyl,
  $NO_2$,
  halogen,
  $OR^5$ wherein $R^5$ is hydrogen or alkyl,
  CN,
  $CO_2R^5$ wherein $R^5$ is as defined above,
  $SO_3R^5$ wherein $R^5$ is as defined above,
  $COR^5$ wherein $R^5$ is as defined above,
  $CONHR^5$ wherein $R^5$ is as defined above, or
  $NHCOR^5$ wherein $R^5$ is as defined above,
2-naphthyl, or
heteroaryl
wherein heteroaryl is selected from the group consisting of: 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl 1H-indol-6-yl, 1H-indol-5-yl, 1H-benzimidazol-6-yl or 1H-benzimidazol-5-yl;
$R^1$ is selected from the group consisting of: hydrogen
  methyl,
  ethyl,
  NO2,
  halogen,
  $OR^5$ wherein $R^5$ is as defined above,
  CN,
  $CO_2R^5$ wherein $R^5$ is as defined above,
  $SO_3R^5$ wherein $R^5$ is as defined above, or
  $COR^5$ wherein $R^5$ is as defined above;
$R^2$ and $R^3$ are the same or different and are independently selected from the group consisting of:
  hydrogen,
  alkyl,
  —$(CH_2)_v$-aryl wherein v is an integer from 1 to 5 and aryl is selected from the group consisting of:

phenyl, phenyl substituted by 1 to 4 substituents selected from the group consisting of:
  alkyl, alkoxy, thioalkoxy, hydroxy, halogen, trifluoromethyl, amino, akylamino, dialkylamino, nitro,
  cyano, carboxy, $SO_3H$, CHO,

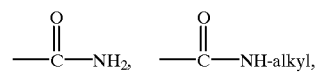

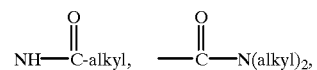

—$(CH_2)n^2$—$NH_2$ wherein $n^2$ is an integer of 1 to 5, —$(CH_2)n^2$—NH-alkyl wherein $n^2$ is as defined above, —$(CH_2)n^2$—$N(alkyl)_2$ wherein $n^2$ is as defined above,
—$(CH_2)_v$-heteroaryl wherein v and heteroaryl are as defined above,
—$(CH_2)_v$-cycloalkyl wherein v is as defined above,
—$(CH_2)_p$—X—$(CH_2)_q$-aryl wherein X is O or S, p and q are each zero or an integer of 1 to 5, and the sum of p+q is not greater than an integer of 5, and aryl is as defined above,
—$(CH_2)_p$—X—$CH_2)_q$-heteroaryl wherein X, p, q and heteroaryl are as defined above,
—$(CH_2)_tNR^6R^{6a}$, wherein t is zero or an integer of from 1 to 9 and $R^6$ and $R^{6a}$ are each the same or different and are as defined above for $R^5$,
—$(CH_2)_vSR^5$, wherein $_v$ and $R^5$ are as defined above,
—$(CH_2)_vCO_2R^5$, wherein $_v$ and $R^5$ are as defined above, or
—$(CH_2)_vCONR^6R^{6a}$, wherein $R^6$ and $R^{6a}$ are the same or different and are as defined above for $R^5$ and v is as defined above;
$R^3$ is additionally —$(CH_2)_rR^7$ wherein r is an integer from 1 to 5 and $R^7$ is 1,3-dihydro-1,3-dioxo-2H-isoindol-2-yl, or 1,3,-dihydro-1,3-dioxobenzoisoindol-2-yl;
Y is CH;

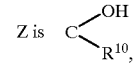

wherein $R^{10}$ is a defined above for $R^2$ and $R^3$, and is independently the same or different from $R^2$ and $R^3$ provided that when Z is

then $R^4$ must be OH,
  C=O,
  C=$NOR^5$ wherein $R^5$ is as defined above, or
  C=N—$NR^6R^{6a}$ wherein $R^6$ and $R^{6a}$ are the same or different and are as defined above for $R^5$;

W is —CHR$^5$ wherein R$^5$ is as defined above;
n is zero or an integer of 1;
R$^4$ is OH;
NR$^6$R$^{6a}$ wherein R$^6$ and R$^{6a}$ are the same of different and are as defined above for R$^5$, when R$^4$ is NR$^6$R$^{6a}$ then Z must be C=O or
NHOR$^9$ wherein R$^9$ is hydrogen, alkyl, or benzyl;
and corresponding isomers thereof; or a pharmaceutically acceptable salt thereof.

2. A compound according to claim 1 wherein Ar is phenyl; and corresponding isomers thereof; or a pharmaceutically acceptable salt thereof.

3. A compound according to claim 1 wherein Z is C=O; and corresponding isomers thereof; or a pharmaceutically acceptable salt thereof.

4. A compound according to claim 1 wherein n is zero; and corresponding isomers thereof; or a pharmaceutically acceptable salt thereof.

5. A compound according to claim 4 wherein R$^1$, R$^2$, and R$^3$ are hydrogen; and corresponding isomers thereof; or a pharmaceutically acceptable salt thereof.

6. A compound according to claim 1 wherein R$^4$ is OH; and corresponding isomers thereof; or a pharmaceutically acceptable salt thereof.

7. A compound according to claim 2 wherein Z is C=NOR$^5$; and corresponding isomers thereof; or a pharmaceutically acceptable salt thereof.

8. A compound which is selected from the group consisting of:
4-Oxo-4-[4-(4-phenyl-piperidin-1-yl)-phenyl]-butyric acid;
4-Oxo-4-[4-(4-phenyl-piperidin-1-yl)-phenyl]-butyric acid, potassium salt;
N-Hydroxy-4-oxo-4-[4-(4-phenyl-piperidin-1-yl)-phenyl]-butyramide;
E/Z-4-Hydroxyimino-4-[4-(4-phenyl-piperidin-1-yl)-phenyl]-butyric acid;
E/Z-4-Benzyloxyimino-4-[4-(4-phenyl-piperidin-1-yl)-phenyl]-butyric acid;
4-Oxo-4-[4-(4-phenyl-piperazin-1-yl)-phenyl]-butyric acid; and
(±)3-Methyl-5-oxo-5-[4-(4-phenyl-piperidin-1-yl)-phenyl]-pentanoic acid.

9. A compound which is 4-oxo-4-[4-(4-phenyl-piperidin-1-yl)-phenyl]-butyric acid.

10. A method of treating arthritis comprising administering to a host suffering therefrom a therapeutically effective amount of a compound according to claim 1 in unit dosage form.

11. A pharmaceutical composition comprising a compound according to claim 1 in admixture with a pharmaceutically acceptable excipient, diluent, or carrier.

12. A method for preparing a compound having the Formula Ia

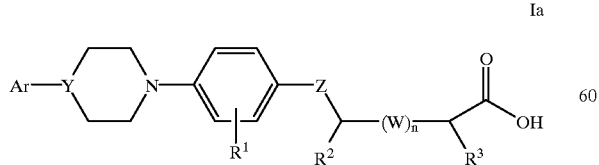

Ia wherein Ar is selected from phenyl,
phenyl substituted with alkyl,
NO$_2$,
halogen,
OR$^5$ wherein R$^5$ is hydrogen or alkyl,
CN,
CO$_2$R$^5$ wherein R$^5$ is as defined above,
SO$_3$R$^5$ wherein R$^5$ is as defined above,
COR$^5$ wherein R$^5$ is as defined above,
CONHR$^5$ wherein R$^5$ is as defined above, or
NHCOR$^5$ wherein R$^5$ is as defined above,
2-naphthyl, or
heteroaryl;
wherein heteroaryl is selected from the group consisting of: 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl or 1H-benzimidazol-5-yl;
R$^1$ is selected from the group consisting of: hydrogen
methyl,
ethyl,
NO$_2$,
halogen,
OR$^5$ wherein R$^5$ is as defined above,
CN,
CO$_2$R$^5$ wherein R$^5$ is as defined above,
SO$_3$R$^5$ wherein R$^5$ is as defined above, or
COR$^5$ wherein R$^5$ is as defined above,
R$^2$ and R$^3$ are the same or different and are independently selected from the group consisting of:
hydrogen,
alkyl
—(CH$_2$)$_v$-aryl wherein v is an integer from 1 to 5 and aryl is selected from the group consisting of: phenyl, phenyl substituted by 1 to 4 substituents selected from the group consisting of: alkyl, alkoxy, thioalkoxy, hydroxy, halogen, trifluoromethyl, amino, alkylamino, dialkylamino, nitro,
cyano, carboxy, SO$_3$H, CHO,

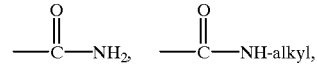

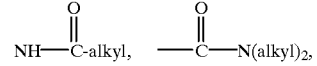

—(CH$_2$)n$^2$—NH$_2$ wherein n$^2$ is an integer of 1 to 5, —(CH$_2$)n$^2$—NH-alkyl wherein n$^2$ is as defined above, —(CH$_2$)n$^2$—N(alkyl)$_2$ wherein n$^2$ is as defined above,
—(CH$_2$)$_v$-heteroaryl wherein v and heteroaryl are as defined above,
—(CH$_2$)$_v$-cycloalkyl wherein v is as defined above,
—(CH$_2$)$_p$—X—(CH$_2$) q-aryl wherein X is O or S, p and q are each zero or an integer of 1 to 5, and the sum of p+q is not greater than an integer of 5, and aryl is as defined above,
—(CH$_2$)$_p$—X—CH$_2$)q-heteroaryl wherein X, p, q and heteroaryl are as defined above,
—(CH$_2$)$_t$NR$^6$R$^{6a}$, wherein t is zero or an integer of from 1 to 9 and R$^6$ and R$^{6a}$ are each the same or different and are as defined above for R$^5$, —$(CH_2)_vSR^5$, wherein $v$ and $R^5$ are as defined above,
—$(CH_2)_vCO_2R^5$, wherein $v$ and $R^5$ are as defined above, or
—$(CH_2)_vCONR^6R^{6a}$, wherein $R^6$ and $R^{6a}$ are the same or different and are as defined above for $R^5$ and v is as defined above;

$R^3$ is additionally —$(CH_2)_rR^7$ wherein r is an integer from 1 to 5 and $R^7$ is 1,3-dihydro-1,3-dioxo-2H-isoindol-2-yl, or 1,3,-dihydro-1,3-dioxobenzoisoindol-2-yl;

Y is CH;
Z is

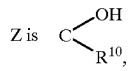

wherein $R^{10}$ is a defined above for $R^2$ and $R^3$, and is independently the same or different from $R^2$ and $R^3$ provided that when Z is

then $R^4$ must be OH,
C=O,
C=$NOR^5$ wherein $R^5$ is as defined above, or
C=N—$NR^6R^{6a}$ wherein $R^6$ and $R^{6a}$l are the same or different and are as defined above for $R^5$;
W is —$CHR^5$ wherein $R^5$ is as defined above;
n is zero or an integer of 1; and corresponding isomers thereof; or a pharmaceutically acceptable salt thereof may be prepared by reacting a compound of Formula II

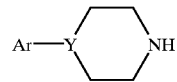

wherein Ar and Y are as defined above with a compound of Formula III

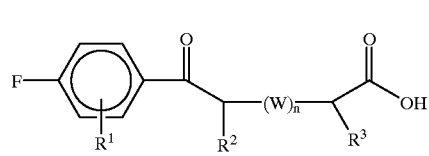

wherein W, n, $R^1$, $R^2$, and $R^3$ are as defined above under basic conditions using conventional methodology to afford a compound of Formula Ia and, if desired, converting a compound of Formula Ia to a pharmaceutically acceptable salt of a compound of Formula Ia by conventional methodology and, if further desired, converting the obtained pharmaceutically acceptable salt of a compound of Formula Ia to a compound of Formula Ia by conventional methodology.

* * * * *